United States Patent [19]

Lachocki

[11] Patent Number: 5,563,251
[45] Date of Patent: Oct. 8, 1996

[54] PROCESS FOR MAKING SURFACTANTS

[75] Inventor: Thomas M. Lachocki, Austin, Tex.

[73] Assignee: CONDEA Vista Company, Houston, Tex.

[21] Appl. No.: 638,342

[22] Filed: Jan. 7, 1991

[51] Int. Cl.$^6$ .......... C07H 15/00; C07H 13/02; C07H 15/04; C07G 3/00
[52] U.S. Cl. .......... 536/18.3; 536/18.6; 536/18.5; 536/119; 536/120; 536/124; 536/123.1; 536/127
[58] Field of Search .......... 536/18.3, 18.6, 536/119, 120, 127, 18.4, 124, 123.1, 18.5; 524/183

[56] References Cited

U.S. PATENT DOCUMENTS

| | | | |
|---|---|---|---|
| 3,585,185 | 6/1971 | Levis et al. | 536/18.6 |
| 3,852,314 | 12/1974 | Hamanaka et al. | 524/183 |
| 4,430,247 | 2/1984 | Austin et al. | 536/18.4 |
| 4,446,313 | 5/1984 | Dix et al. | 536/120 |
| 4,767,846 | 8/1988 | Stepto et al. | 536/18.3 |
| 4,834,903 | 5/1989 | Roth et al. | 536/18.3 |
| 5,006,648 | 4/1991 | Van der Plank et al. | 536/119 |

FOREIGN PATENT DOCUMENTS

| | | | |
|---|---|---|---|
| 0219204 | 2/1985 | Germany | 536/18.3 |

*Primary Examiner*—John Kight
*Assistant Examiner*—Louise N. Leary
*Attorney, Agent, or Firm*—Browning Bushman

[57] ABSTRACT

A process for producing a nonionic surfactant wherein a polyol, e.g. a saccharide, is introduced into a reaction vessel, a mixture of an alkylene oxide containing from about 2 to about 5 carbon atoms and a lipophilic compound containing an epoxide group and having at least 6 carbon atoms is introduced into the reaction vessel, the polyol and the mixture being reacted in the presence of a catalyst and under conditions such that the rate of introduction of the mixture into the reaction vessel is controlled by the rate of reaction between the alkylene oxide and the polyol, the reaction between the polyol and the mixture being conducted at a temperature above the boiling point of the alkylene oxide.

20 Claims, No Drawings

PROCESS FOR MAKING SURFACTANTS

BACKGROUND OF THE INVENTION

1. Field of the Invention

The present invention relates to nonionic surface active compounds and, more particularly, to a process for producing surfactants from polyols and certain epoxy compounds.

2. Background of the Invention

Nonionic surface active agents formed by the reaction of certain polyols, i.e. compounds containing at least two hydroxyl groups, and epoxy compounds are well known. For example, surfactants which are resistant to hydrolysis can be made by reacting polyols with epoxy alkanes in the presence of a catalyst and with heating.

One problem that has been encountered with the reaction between polyols and epoxy compounds is that being respectively hydrophilic and hydrophobic in nature, these materials form two phases hindering reaction. One solution to this problem has been to conduct the reaction in a solvent in which the polyol and the epoxy compound have sufficient mutual solubility. However, the use of a solvent in the reaction requires an extra separation step as the solvents are generally skin irritants and/or incompatible with products made from the surfactants.

SUMMARY OF THE INVENTION

It is therefore and object of the present invention of providing an improved process for producing nonionic surfactants.

Another object of the present invention is to provide a process for reacting hydrophilic polyols with hydrophobic epoxy compounds to produce nonionic surfactant compounds.

Yet another object of the present invention is to provide a process for reacting hydrophilic polyols with hydrophobic epoxy compounds in which polymerization of the epoxy compound is minimized.

The above and other objects of the present invention will become apparent from the drawings, the description given herein and the appended claims.

The process of the present invention involves reacting a polyol with a mixture of (1) an alkylene oxide having from about 2 to about 6 carbon atoms and (2) a lipophilic compound having an epoxide linkage and containing at least about 6 carbon atoms, the reaction being carried out by introducing the polyol into a suitable reaction vessel and subsequently introducing the mixture of the alkylene oxide and the lipophilic compound into the reaction vessel, the rate of introduction of the mixture into the reaction vessel being controlled as a function of the reaction of the alkylene oxide with the polyol, the reaction being carried out in the presence of a suitable catalyst. The reaction is conducted at a temperature greater than the boiling point of the alkylene oxide.

DESCRIPTION OF THE PREFERRED EMBODIMENT

The process of the present invention possesses several advantages over prior art processes for the reaction of hydrophilic polyols with hydrophobic (lipophilic) epoxy compounds. Of their nature, hydrophilic polyols and hydrophobic epoxy compounds do not readily react because they form biphasic mixtures due to their extreme differences in polarity. It has now been found that the phase separation problem can be overcome if a mixture of a low molecular weight epoxy compound and the lipophilic epoxy compound is reacted with the hydrophilic polyol under certain conditions. More specifically, the use of a mixture of a low molecular weight epoxy compound(s), having moderate polarity and lipophilic epoxy compound(s) having low polarity results in the formation of a homogeneous (monophasic) product mixture. Moreover, epoxide polymerization which is often present when high concentrations of epoxy compounds are present in the reaction vessel is minimized, a desirable result since such polymerization yield hydrophobic polyepoxides with concomitant lower yields of the desired surfactant compounds.

A wide variety of hydrophilic polyols are useful in the process of the present invention and can include, without limitation, diols (e.g. ethylene glycol, propylene glycol, etc.), triols (e.g. glycerol, butanetriol, etc.), tetraols (e.g. erythritol, threitol, pentaerythritol, etc.), pentaols (e.g. xylitol, arabitol, ribitol, etc.), hexaols (e.g. sorbitols, mannitol, galactitol, etc.), aldo- or keto-triose, -tetrose, -pentaose, -hexose, -heptose, etc. (e.g. glyceraldehyde, erythrose, threose, ribose, arabinose, fructose, sorbose, glucose, galactose, mannose), di-, tri-, oligo- or polysaccharides, such as sucrose, cellobiose, isomaltose, maltose, maltotriose, starch, cellulose, hemicellulose, etc. Additionally, non-reducing sugars derived from mono-, di-, tri-, oligo- or polysaccharides, e.g. alkyl glycosides like methyl-glycoside, other sugars such as trehalose, isotrehalose, raffinose, stachyose, etc.) can also be used. Other useful polyols include aldonic acid, aldonic acid salts (e.g. methyl gluconate, sodium gluconate, etc.), aldonic lactones (e.g. gluconolactone, etc.), aldaric acid esters or salts (e.g. dimethyltartarate, diamonium tartarate, etc.). Also, mixtures of any of the above polyols may be used. The polyols that are useful in the process of the present invention can also include polyols as mentioned above which have been reacted with ethylene oxide or other alkylene oxides to provide alkoxylated polyols with reactive hydroxyl groups which can react with the mixture of the alkylene oxide and the lipophilic epoxy compounds. Especially preferred are polyols having an average number of hydroxyl groups of from about 3 to about 10.

The low molecular weight epoxy compounds used in the process of the present invention are those alkylene oxides containing from about 2 to about 5, especially from about 2 to about 4 carbon atoms. Non-limiting examples of such compounds includes ethylene oxide, propylene oxide, butylene oxide, pentylene oxide, 1,2-epoxybutylene, 2,3-epoxybutylene, 2-methyl-2,3-epoxybutylene, etc. The alkylene oxides may be used as pure compounds or in mixtures to tailor the properties of the surfactant.

The hydrophobic epoxy compounds, i.e. the lipophilic epoxy compounds, can also be a pure compound or a mixture of compounds, will contain at least 6 carbon atoms, preferably 8 to 30 carbon atoms, and will contain an epoxide linkage. The lipophilic epoxy compounds can be mono-, di- or trisubstituted. Non-limiting examples of such lipophilic compounds include alpha-olefin epoxy compounds such as hexylene oxide, heptylene oxide, octylene oxide, etc. or glycidyl ethers, such as phenyl glycidyl ether, octyl glycidyl ether, decyl glycidyl ether, epoxides of unsaturated fats, oils, fatty acids, salts or fatty esters, internal-olefin epoxides, cyclododecyl epoxide, etc., branched internal-olefin epoxides, etc. Quaternary substituted epoxides can also be used.

The reaction between the polyol and the mixture of epoxy compounds can be conducted as a one-pot, solvent-free reaction in the presence of a suitable catalyst and, if desired, in the presence of an inert gas, such as nitrogen, argon, helium, etc. In a preferred method of carrying out the process, polyol(s) and catalysts are added to a reactor. Alternatively, the catalyst can be mixed or dissolved in the mixture of the epoxy compounds. The reactor containing the polyols is heated to the desired temperature, oxygen and water being removed by purging with an inert gas, such as nitrogen. The mixture of the alkylene oxide and the lipophilic compound is suitably contained in a separate vessel, preferably the mixture being purged with an inert gas, such as nitrogen. Once water and oxygen have been removed from the reaction vessel containing the polyol, addition of the mixture of the alkylene oxide and the lipophilic compound can be conveniently carried out by placing a differential pressure between the reaction vessel and the vessel containing the mixture of the alkylene oxide and the lipophilic compound, the reaction vessel being at a lower pressure. As the mixture of epoxy compounds adds to the reaction vessel, reaction vessel pressure increases until a steady state is set up such that the mixture of epoxy compounds adds to the reaction vessel as the epoxy compounds are consumed. Thus, the rate of introduction of the mixture of the epoxy compounds into the reaction vessel is controlled as a function of the rate of reaction between the alkylene oxide and the polyol. In effect, the mixture of the alkylene oxides and the lipophilic compound acts as a reagent addition "clock." It is also possible for the alkylene oxide and the lipophilic compound to be introduced separately but simultaneously into the reaction vessel, the introduction of the lipophilic compound again being controlled as a function of the rate of reaction between the alkylene oxide and the polyol. Thus, for example, with suitable valving and pressure regulators, separate but simultaneous addition of the alkylene oxide and the lipophilic compound can be achieved, the pressure in the reaction vessel due to the lighter, more volatile alkylene oxide being used to regulate introduction of not only the alkylene oxide but the lipophilic epoxy compound into the reaction vessel.

The reaction temperature in the reaction vessel is a function of the alkylene oxide portion of the mixture to the extent that the reaction temperature must be higher than the boiling point of the alkylene oxide. Generally speaking, the reaction temperature will vary from about 70° C. to about 275° C., more preferably from about 100° C. to about 200° C. The other limitation on temperature is the stability of the polyol. Since, as known to those skilled in the art, numerous polyols do not readily re-crystallize once melted, reaction temperature can be increased to the polyol's melting point and then cooled before the remainder of the reaction is carried out. However, it is to be understood that it is not necessary to melt the polyol before the reaction is started.

The unique process of the present invention wherein the rate of reaction of the alkylene oxide controls the addition rate of the mixture of the alkylene oxide and the lipophilic compound to the reaction vessel ensures that a minimum concentration of epoxy compounds is maintained in the reactor at all times. In other words, concentration control is accomplished because of the volatility of the alkylene oxide, it being remembered that the reaction temperature is maintained at the point above the boiling point of the particular alkylene oxide(s) employed. Accordingly, as the lower molecular weight alkylene oxide is consumed in the reaction, reaction pressure drops. Thus, epoxy compounds are replenished only as they are consumed. Since the vapor pressure of the heavier lipophilic compound(s) is very low at the reaction temperatures, consumption of the lipophilic compound does not appreciably change reaction pressure and therefore has minimal consequential effect on the rate of introduction of the mixture of the alkylene oxide and the lipophilic compound.

Reaction pressures can vary from below atmospheric to several hundred pounds per square inch. As noted above, in a case where the mixture of the alkylene oxide and the lipophilic compound is introduced from a separate vessel simultaneously into the reaction vessel, it is necessary to provide a pressure differential between the reaction vessel and the vessel containing the mixture of the alkylene oxide and the lipophilic compound in order to initiate addition of the mixture of the alkylene oxide and the lipophilic compound to the reaction vessel.

The concentration ratio between the alkylene oxide and the lipophilic compound can vary over a broad range. For example, the weight percent of the alkylene oxide in the mixture of alkylene oxide and lipophilic compound can vary between from about 1 to about 99%, the lower limit being dictated by the alkylene oxide's ability to increase reactor pressure upon addition in the case where reactor pressure controls the feed of the mixture to the reaction vessel. On the other hand, the upper limit is discretionary based on the desired product properties. Accordingly, the percent of the lipophilic compound in the mixture can vary from about 1 to about 99% by weight, and it will be recognized that, as the reaction proceeds, the ratio of the alkylene oxide to the lipophilic compound can be continuously varied to tailor the properties of the desired product. Generally speaking, the total amount of the lipophilic compound relative to the polyol will range from about 0.01 to about 10 equivalents, preferably from about 0.1 to about 5 equivalents, per equivalent of hydroxyl group in the polyol, while the alkylene oxide concentration can range from about 0.01 to about 50 equivalents, more preferably from about 0.1 to 10 equivalents, per hydroxyl group in the polyol.

A wide variety of catalysts can be used to catalyze addition reactions of epoxy compounds and are therefore useful in the process of the present invention. Either basic or acidic catalysts can be employed depending upon the particular polyol(s) chosen. As is well known, basic catalysts are effective for most reactions involving epoxy compound addition. However, a Lewis acid catalyst can be employed, particularly where reducing carbohydrates are used, since reducing carbohydrates are prone to decomposition when heated with bases. Non-limiting examples of suitable basic catalysts include metal, mono-, di-, or tri-hydroxides (e.g. sodium hydroxide, potassium hydroxide, calcium hydroxide, strontium hydroxide), metal alkoxides (e.g. sodium methoxide, potassium-tert-butoxide, etc.), ammonium compounds (e.g. ammonium hydroxide, tetramethylammonium hydroxide, tetramethylammonium hydroxide, dodecyltrimethylammonium hydroxide, etc.), amines (e.g. trimethyl amine, monoethanol amine, triethanol amine, dodecyldimethyl amine, etc.). Suitable non-limiting examples of acid catalysts include boron trifluoride, boron trifluoride etherate, tin (II or IV) chloride, aluminum chloride, iron (III) chloride, titanium (IV) chloride, etc. ). The amount of catalyst employed will range from about 0.1 to about 30 mole percent with respect to the amount of polyol employed.

Although a particularly desirable feature of the process of the present invention is that it can be carried out in the absence of a solvent, solvents can be employed if desired. However, the ability to produce surfactants free of solvents is highly desirable since many solvents commonly used to produce such nonionic surfactants are toxic, present removal problems and often times end up in end products produced from the surfactants resulting in undesirable properties. If desired, materials can be added to stabilize and/or aid in melting of the polyol. For example, antioxidants (e.g. butylated hydroxy toluene or anisol, tocopherols, etc.), low molecular weight polar epoxides (e.g. glycidol, epichlorohydrin, etc.), or other such materials can be added. The addition of surfactants or phase-transfer catalysts is desirable since such compounds aid in lowering interfacial tension between the reactants and increase the reaction rate. For example, it has been found that the product produced by the present process can be used in subsequent reactions to increase the rate of reaction.

The nonionic surfactants produced according to the process of the present invention can be derivatized to produce specifically tailored surfactants. Thus, the surfactants can be ethoxylated, propoxylated, etc. A particularly desirable feature of the present invention is that since the process can be carried out in the absence of solvents, derivatization reactions can be carried out in the reaction vessel without the risk of adding water and interfering with subsequent reactions.

It has been found that nonionic surfactants produced according to the process of the present invention possess color which is comparable to commercial alkylpolyglycocides, i.e. many of the surfactants produced according to the process are light yellow in character minimizing and/or eliminating the need for costly product purification. However, well known purification processes can be used if desired to further enhance product quality. It has also been found that the nonionic surfactants, particularly the hydroxyalkyl polyols, possess greater hydrolytic stability than alkylpolyglycosides or sugar esters. This is believed to be due to the etheric bond formed between the polyol and the hydrophobic hydroxyalkyl group derived from the epoxy mixture, such etheric bonds being stable toward both acids and bases.

To more fully illustrate the present invention, the following non-limiting examples are presented.

EXAMPLE 1

To a reactor fitted with a vacuum line, a nitrogen inlet, a temperature controller, and a lecture bottle was added 40 g of sorbitol (0.22 mole) and 2.0 g of tetramethylammonium hydroxide pentahydrate (0.011 mole). As the reactants were stirred and heated to 100° C., air was replaced with dry nitrogen. After the reactor had reached 100° C., residual water was removed by passing nitrogen through the reactor for 5–10 minutes. The reactor was then quickly heated to between 120°–130° C. To help melt the carbohydrate, the reactor temperature could have been raised to a higher temperature prior to being cooled to 120°–130° C. A mixture of 1,2-epoxybutane (18.8 ml, 0.22 mole) and 1,2-epoxydecane (43.0 ml, 0.22 mole) was added from the lecture bottle to the reactor. Addition of the mixture of epoxy compounds stopped when the reactor head pressure equaled the pressure in the lecture bottle. As the epoxy compounds were consumed, more of the mixture of epoxy compounds were drawn into the reactor due to the pressure drop. At a point when the pressure no longer drops, the reaction is considered complete, the reaction mixture being stirred for a short period of time to ensure reaction completion.

Analysis of the product obtained by gas chromatography and high performance liquid chromatography showed that virtually no free epoxy compounds or polyol remained in the product mixture. NMR analysis suggests that the epoxy compounds may bind to any of the oxygens on the sorbitol.

EXAMPLE 2

To a reactor was added 80.0 g D-sorbitol and 4.0 g tetramethylammonium hydroxide pentahydrate. In a separate metal addition bomb was added 15.8 g of 1,2-epoxybutane and 68.6 g of 1,2-epoxydecane in a nitrogen atmosphere. The reactor was sealed, flushed with nitrogen three times as the reactor was heated to 110° C., and continuously stirred with a mechanical stirrer. Dry nitrogen was drawn through the reactor to remove water as the reactor was heated to the reaction temperature (130° C.). Increased nitrogen pressure in the addition bomb forced some of the mixture of epoxy compound into the reactor. Addition of the mixture continued as the mixture of epoxy compound in the reactor was consumed.

A light yellow viscous liquid resulted that showed moderate solubility in water and acetone. Good surface active properties were observed. A stable, thick foam was observed when a 1% solution of the crude product was shaken in water.

An optional purification procedure was performed to remove nonpolar by-products. 154 g of crude product was dissolved in methanol and extracted with hexane (2×250 ml). Approximately 145 g of purified product were recovered. Optional purification procedures used activated charcoal and ion exchange resins to improve color or remove catalyst. Optionally, the catalyst can be neutralized and filtered from the product.

EXAMPLE 3

As in Example 1, 65 g of D-sorbitol and 2.7 g tetramethylammonium hydroxide pentahydrate were reacted with a mixture of 26.0 g of 1,2-epoxybutane and 66.4 g of 1,2-epoxydodecane. The golden viscous liquid that resulted showed appreciable water and acetone solubility and yielded foam when shaken in water.

As in Example 1, product was dissolved in methanol and extracted with hexane. The purified product, which was diluted to 8 and 150 ppm, yielded surface tensions of 32.8 and 26.9 dyne/cm$^2$, respectively.

EXAMPLE 4

As in Example 1, 65.6 g of D-sorbitol and 2.7 g tetramethylammonium hydroxide pentahydrate were reacted with a mixture of 16.0 g of 1,2-epoxybutane and 81.0 g of 1,2-epoxydodecane. The golden viscous liquid that resulted showed appreciable water and acetone solubility and yielded foam when shaken in water.

As in Example 1, product was dissolved in methanol and extracted with hexane. The purified product, which was diluted to 5 and 80 ppm, yielded surface tensions of 42.9 and 24.9 dyne/cm$^2$, respectively.

EXAMPLE 5

As in Example 1, 40.0 g of D-sorbitol and 2.0 g tetramethylammonium hydroxide pentahydrate were reacted with a mixture of 15.8 g of 1,2-epoxybutane and 63.0 g of glycidyl ether. The glycidyl ether was a mixture that was derived from decanol (2.5%), dodecanol (67.5%) tetradecanol (24.6%), and hexadecanol (5.6%). The yellow viscous liquid that resulted showed appreciable water and acetone solubility and yielded foam when shaken in water.

As in Example 1, the product was dissolved in methanol and extracted with hexane. The purified product that was diluted to 10 and 100 ppm yielded surface tensions of 33.9 and 31.1 dyne/cm$^2$, respectively.

EXAMPLE 6

As in Example 1, 70 g of sorbitol and 0.8 g of sodium hydroxide pellets, which had been crushed, were reacted with a mixture of 27.7 g of 1,2-epoxybutane and 88.4 g of 1,2-epoxydodecane. A sample of the yellow viscous liquid that resulted produced a stable foam when shaken with water.

Subsequently, 84.5 g of ethylene oxide were added to the reactor. The orange syrup that resulted exhibited improved water solubility and foam volume than the non-ethoxylated product. The crude product, which was diluted to 10 ppm, yielded surface tensions of 29 dyne/cm$^2$.

EXAMPLE 7

As in Example 1, 80.0 g of Maltitol and 0.5 g sodium hydroxide pellets that were crushed were reacted with a mixture of 16.7 g of 1,2-epoxybutane and 42.8 g of 1,2-epoxydodecane. The yellow liquid that resulted turned into a sticky solid around room temperature. This product showed lower acetone solubility and higher water solubility than the corresponding sorbitol product. The product foamed in water.

As in Example 1, the product was dissolved in methanol and extracted with hexane. The purified product, which was diluted to 100 ppm, yielded surface tensions of 30.94 dyne/cm$^2$.

EXAMPLE 8

As in Example 1, 60.0 g of Maltitol and 0.35 g sodium hydroxide pellets that were crushed were reacted with a mixture of 20.2 g of 1,2-epoxypropane and 50.0 g of glycidyl ether based on dodecanol (55%) and tetradecanol (45%). The whitish-yellow liquid that resulted turned into a sticky solid around room temperature. This product, which foamed in water, showed lower acetone solubility than the corresponding sorbitol product. The crude product, which was diluted to 10 and 100 ppm, yielded surface tensions of 41 and 32 dyne/cm$^2$, respectively.

EXAMPLE 9

As in Example 1, 22.5 g of sucrose, 12.0 g of sorbitol, and 0.5 g sodium hydroxide pellets that were crushed were reacted with a mixture of 11.3 g of 1,2-epoxybutane and 28.7 g of 1,2-epoxydodecane. The reddish brown liquid that resulted was dissolved in a minimal amount of methanol and extracted with hexane (2×250 ml). After most of the volatile solvents were removed (8% methanol remained), a viscous brown liquid resulted that produced a stable foam after shaken with water. The purified product, which was diluted to 10 and 100 ppm, yielded surface tensions of 27.2 and 27.8 dyne/cm$^2$, respectively.

EXAMPLE 10

As in Example 1, 40.0 g of sucrose, which was blended into a fine powder, 1.7 g of glycidol, and 1.0 g of tetramethylammonium hydroxide pentahydrate were reacted with a mixture of 6.8 g of 1,2-epoxypropane and 21.5 g of 1,2-epoxydodecane. The tan sticky solid that resulted produced a foam when shaken with water. The crude product diluted to 10 and 100 ppm yielded surface tensions of 29.1 and 11.7 dyne/cm$^2$, respectively.

EXAMPLE 11

As in Example 1, 195 g of methyl glucopyranoside and 2.0 g of sodium hydroxide pellets that were crushed were reacted with a mixture of 58.3 g of 1,2-epoxybutane and 185.1 g of 1,2-epoxydodecane. A sample of the reddish brown liquid that resulted produced a stable foam when shaken with water.

A sample of the products (95 g) that still contained base was reacted with an additional 47.9 g of ethylene oxide. The brown syrup that resulted exhibited improved water solubility and improved foam volume when shaken with water.

EXAMPLE 12

As in Example 1, 92.1 g of glycerol and 2.0 g of sodium hydroxide pellets, which were crushed, were reacted with a mixture of 58.3 g of 1,2-epoxypropane and 230 g of glycidyl ether. The glycidyl ether was a mixture that was derived from octanol (42.5% ) and decanol (57.5%). The yellow liquid that resulted exhibited high acetone solubility and some foam when shaken in water.

The crude product, which was diluted to 10 and 100 ppm, yielded surface tensions of 32 and 28 dyne/cm$^2$, respectively.

EXAMPLE 13

As in Example 1, 40.0 g methyl-glucopyranoside and 1.2 g potassium hydroxide pellets that were crushed were reacted with a mixture of 18.1 g of ethylene oxide and 45.3 g of glycidyl ether at 170° C. The glycidyl ether was a mixture that was derived from octanol (42.5%) and decanol (57.5%).

A yellow viscous liquid resulted. A stable thick foam was observed when a 1% solution of the crude product was shaken in water.

EXAMPLE 14

40.0 g sorbitol and 0.9 g sodium hydroxide pellets that were crushed were reacted with 48.3 g of ethylene oxide. The products of this reaction were reacted as in Example 1 with a mixture of 38.3 g of propylene oxide and a mixture of 1,2-hexadecyl epoxide (26.3 g) and 1,2-octadecylepoxide (29.4 g) at 180° C.

A yellow viscous liquid cooled into a solid. A stable thick foam was observed when a 1% solution of the crude product was shaken in water. This example illustrates the use of an ethoxylated polyol produced from another polyol, i.e. sorbitol, which has been reacted with ethylene oxide to form the starting polyol in the reaction according to the process of the present invention.

As can be seen from the above examples, the process of the present invention provides a one-step method for producing nonionic surfactants from polyols and epoxy-type compounds. The process can be carried out in a single vessel, in the absence of a solvent, and utilizes the volatility of the alkylene oxide to control the addition of the mixture of the alkylene oxide and the lipophilic compound to the reactor vessel thereby minimizing formation of polyepoxides. As noted, an especially desirable feature of the process is that it can be conducted in the absence of a reaction solvent, since the mixture of the alkylene oxide and the lipophilic compound, simultaneously with the polyol, solves the phase separation problem which has long plagued attempts to react hydrophilic materials, i.e. polyols, with lipophilic materials, i.e. epoxy compounds containing 6 or greater carbon atoms, preferably 10 or more carbon atoms.

The nonionic surfactants made by process of the present invention can be formulated with one or more surface active agents selected from anionic, nonionic, zwitterionic, amphoteric and cationic classes and compatible mixtures thereof.

The anionic surfactants may have counterions that include, although are not limited to, alkali cations (e.g. sodium, potassium, etc.), alkaline earth cations (magnesium, calcium, etc.) or nitrogen-derived counterions (e.g. ammonium, alkylolammonium). Suitable amines include, but are not limited to, trimethylamine, triethanol amine, monoethanol amine, etc. Non-limiting examples of suitable anionic surfactants include: salts of the higher fatty acids (i.e. soaps) with alkyl chains from about 8 to 18 carbon atoms; alkylbenzene and alkylaryl sulfonates with alkyl chains from about 9 to 15 carbon atoms; alcohol sulfates with alkyl chains from about 8 to 18 carbon atoms; alcohol ethoxylate sulfates with about 1 to 20 ethylene oxide units per molecule and with alkyl chains from about 8 to 18 carbon atoms; alkyl phenol ethoxylate sulfates with about 1 to 20 ethylene oxide units per molecule and with alkyl chains from about 8 to 12 carbon atoms; alpha-sulfonated fatty acids (or esters) containing from about 6 to 20 carbon atoms in the fatty acid group and about 1 to 18 carbon atoms in the ester group; and olefin or paraffin sulfonates containing from about 10 to 20 carbon atoms. Other anionic surfactants include: alkyl glyceryl ether sulfonates, sulfosuccinates, phosphate esters, alkyl isethionates, acyl sarcosides, alkyl taurides, etc.

Non-limiting examples of nonionic surfactants include: alcohol ethoxylates with alkyl groups from about 8 to 22 carbon atoms and from about 2 to 12 ethylene oxide groups per molecule, and alkyl phenol ethoxylates with alkyl groups from about 6 to 16 carbon atoms and from about 2 to 12 ethylene oxide groups per molecule. Other nonionics include: polyglycosides, alkylolamides, sucrose esters, alkyl polyglycosides, sorbitan esters, nonionic block copolymers, and fatty amine oxides.

Non-limiting examples of cationic surfactants include quaternary ammonium salts.

Non-limiting examples of amphoteric and zwitterionic surfactants include sulfobetaines, imidazoline-derived betaines, alkyl amidopropylbetaines, etc.

The nonionic surfactants described herein may be formulated with one or more surface active agents described above as well as builders, anti-redeposition agents, enzymes, bleaching agents, brighteners or dyes, polymers and/or hydrotropes, etc.

Formulated products employing surfactants made according to the process of the present invention include, but are not limited to, heavy duty detergent liquids, or powders, concentrated liquid and powdered detergents, light duty liquids, shampoos, emulsifiers, cosmetic cleaners, soap bars, alkaline cleaner formulations, acidic cleaner formulations, lubricants, industrial processing aids, rinse aids, hard surface cleaners, etc.

What is claimed is:

1. A process for producing a surfactant compound comprising the steps of:

introducing a hydrophilic polyol into a reaction vessel;

introducing a mixture of (a) an alkylene oxide having from 2 to about 5 carbon atoms and (b) a lipophilic compound having an epoxide group and having at least 6 carbon atoms into said reaction vessel, the rate of introduction of said mixture into said reaction vessel being controlled by the rate of reaction between said alkylene oxide and said polyol; and reacting said polyol and said mixture in the presence of a catalyst and at a temperature above the boiling point of said alkylene oxide.

2. The process of claim 1 wherein said reaction is conducted at a temperature of from about 70° C. to about 275° C.

3. The process of claim 2 wherein said reaction is conducted at a temperature of from about 100° to about 200° C.

4. The process of claim 1 wherein said reaction is conducted in the presence of an inert gas.

5. The process of claim 1 wherein said catalyst is a base.

6. The process of claim 1 wherein said alkylene oxide is present in said mixture in an amount of from about 1 to about 99% by weight.

7. The process of claim 1 wherein the amount of said lipophilic compound ranges from about 0.01 to about 10 equivalents per hydroxyl group in said polyol.

8. The process of claim 1 wherein the amount of said alkylene oxide ranges from about 0.01 to about 50 equivalents per hydroxyl group in said polyol.

9. The process of claim 1 wherein said mixture of said alkylene oxide and said lipophilic compound is initially present in a second vessel, said second vessel being at a higher pressure than said reaction vessel, said mixture being introduced into said reaction vessel in response to differential pressure between said second vessel and said reaction vessel.

10. A nonionic surfactant produced by the process of claim 1.

11. The process of claim 4 wherein said inert gas is selected from the group consisting of nitrogen, the noble gases and mixtures thereof.

12. The process of claim 1 wherein said reaction is conducted in the absence of a solvent.

13. The process of claim 6 wherein said lipophilic compound is present in said mixture in an amount of from about 1 to about 99% by weight.

14. The process of claim 1 wherein said polyol is selected from the group consisting of polyols having from about 3 to about 10 hydroxyl groups and mixtures thereof.

15. The process of claim 1 wherein said polyol is selected from the group consisting of diols, triols, tetraols, pentaols, hexaols, heptaols, aldo-trioses, aldo-tetroses, aldo-pentaoses, aldo-hexoses, aldo-heptoses, keto-trioses, keto-tetroses, keto-pentaoses, keto-hexoses, keto-heptoses, disaccharides, trisaccharides, oligosaccharides, polysaccharides, non-reducing sugars derived from said saccharides, aldonic acid, aldonic acid salts, aldonic lactones, aldaric acid esters, aldaric acid salts and mixtures thereof.

16. The process of claim 1 wherein said alkylene oxide is selected from the group consisting of alkylene oxides having from 2 to 4 carbon atoms and mixtures thereof.

17. The process of claim 1 wherein said lipophilic compound has from 6 to about 30 carbon atoms.

18. The process of claim 1 wherein said lipophilic compound is selected from the group consisting of alpha-olefin epoxy compounds, glycidyl ethers, internal-olefin epoxides, branched internal-olefin epoxides, quaternary substituted epoxides and epoxides of unsaturated fats, oils, fatty acids, salts and fatty esters and mixtures thereof.

19. The process of claim 5 wherein said catalyst is selected from the group consisting of metal hydroxides, metal alkoxides, ammonium compounds and amines.

20. The process of claim 1 wherein said catalyst is selected from the group consisting of sodium hydroxide, potassium hydroxide, calcium hydroxide, strontium hydroxide, sodium methoxide, potassium-tert-butoxide, ammonium hydroxide, tetramethylammonium hydroxide, dodecyltrimethylammonium hydroxide, trimethylamine, monoethanol amine, triethanol amine, dodecyldimethylamine, boron trifluoride, boron trifluoride etherate, tin(II or IV chloride), aluminum chloride, iron(III)chloride and titanium(IV)chloride.

* * * * *